(12) United States Patent
Placier et al.

(10) Patent No.: US 10,195,276 B2
(45) Date of Patent: Feb. 5, 2019

(54) METHOD FOR THE PRODUCTION OF HYDROLYZED ALLERGENS

(75) Inventors: Gael Placier, Brussels (BE); Laetitia Frisch, Pecq (BE); Thierry Legon, Korbeek Lo (BE); Marie-Ange Benoit, Vedrin (BE)

(73) Assignee: BIOTECH TOOLS S.A., Brussels (BE)

( * ) Notice: Subject to any disclaimer, the term of this patent is extended or adjusted under 35 U.S.C. 154(b) by 263 days.

(21) Appl. No.: 14/125,036

(22) PCT Filed: Jun. 15, 2012

(86) PCT No.: PCT/EP2012/061404
§ 371 (c)(1),
(2), (4) Date: Apr. 16, 2014

(87) PCT Pub. No.: WO2012/172037
PCT Pub. Date: Dec. 20, 2012

(65) Prior Publication Data
US 2014/0220044 A1    Aug. 7, 2014

(30) Foreign Application Priority Data
Jun. 15, 2011 (EP) .................................. 11170031

(51) Int. Cl.
| | |
|---|---|
| *A21D 2/26* | (2006.01) |
| *A61K 45/06* | (2006.01) |
| *A61K 39/00* | (2006.01) |
| *A61K 39/35* | (2006.01) |
| *C07K 14/415* | (2006.01) |
| *C12P 21/06* | (2006.01) |
| *C07K 14/435* | (2006.01) |

(52) U.S. Cl.
CPC .............. *A61K 45/06* (2013.01); *A61K 39/00* (2013.01); *A61K 39/35* (2013.01); *C07K 14/415* (2013.01); *C07K 14/43531* (2013.01); *C12P 21/06* (2013.01)

(58) Field of Classification Search
None
See application file for complete search history.

(56) References Cited

U.S. PATENT DOCUMENTS 5,039,532 A    8/1991    Jost et al.
2009/0324650 A1*  12/2009 Legon .................... A61K 39/35
424/275.1

FOREIGN PATENT DOCUMENTS

| JP | H02-2319 A | 1/1990 |
|---|---|---|
| JP | 2002-249442 A | 9/2002 |
| JP | 2010-504278 A | 2/2010 |

| WO | WO-02/20559 | 3/2002 |
|---|---|---|
| WO | WO-2008/000783 | 1/2008 |
| WO | WO-/2009/083589 | 7/2009 |

OTHER PUBLICATIONS

Hildebrandt et al. 'In Vitro Determination of the Allergenic Potential of Technologically Altered Hen's Egg.' J. Agric. Food Chem. 56:1727-1733, 2008.*
Von Boxtel et al. 'Legumin allergens from peanuts and soybeans: Effects of denaturation and aggregation on allergenicity.' Mol. Nutr. Food Res 52:674-682, 2008.*
Van Boxtel et al., "Legumin allergens from peanuts and soybeans: Effects of denaturation and aggregation on allergenicity", Mol. Nutr. Food Res. 2008, vol. 52, pp. 674-682.
Communication pursuant to Article 91(3) EPC issued in European Patent Application No. 12 728 495.8-1412, dated Sep. 15, 2015.
Lee et al., "Mass Spectrometry Analysis of Soybean Seed Proteins: Optimization of Gel-Free Quantitative Workflow", Anal. Methods, 2010, pp. 1577-1583, 2.
Houston et al., "Quantitation of Soybean Allergens Using Tandem Mass Spectrometry", Journal of Proteome Research, 2011, pp. 763-773, 10.
Marsh et al., "Purification and Characterisation of a Panel of Peanut Allergens Suitable for Use in Allergy Diagnosis", Mol. Nutr. Food Res., 2008, pp. S272-S285, 52.
Burks et al, "Identification of a Major Peanut Allergen, ARA h I, in Patients With Atopic Dermatitis and Positive Peanut Challenges", pp. 172-179.
Bensadoun et al., "Assay of Proteins in the Presence of Interfering Materials", Analytical Biochemistry, 1976, pp. 241-250, 70.
Jiang et al., "Comparison of Protein Precipitation Methods for Sample Preparation Prior to Proteomic Analysis", Journal of Chromatography A, 2004, pp. 317-320, 1023.
Written Opinion and International Search Report of PCT/EP2012/061404 dated Nov. 7, 2012.
European Search Report of Application No. 11170031.6-2406 dated Mar. 2, 2012.
Ambler et al., "Some Properties of Ascaris suum Allergen A," Int. Arch. Allergy, 1974, vol. 46, pp. 427-437.
Sekul et al., "Some Functional Properties of Peanut Proteins Partially Hydrolyzed with Papain," Partial Hydrolysis of Peanut Proteins with Papain, J. Agric. Food Chem., 1978, vol. 26, No. 4, pp. 855-858.

* cited by examiner

*Primary Examiner* — Nora M Rooney
(74) *Attorney, Agent, or Firm* — Venable LLP; Keith G. Haddaway

(57) ABSTRACT

A method for the production of hydrolyzed allergens from allergens comprising the steps of:
a) extracting a source of allergens comprising allergenic proteins to form an extract,
b) purifying the extract to remove non-protein components to form a purified extract,
c) denaturing the purified extract with a first denaturing agent to form a purified denatured extract,
d) refining the purified denatured extract to remove impurities to form a refined denatured extract,
e) denaturing the refined denatured extract with a second denaturing agent to form denatured allergen mixture, and
f) hydrolyzing the denatured allergen mixture to form the hydrolyzed allergens.

14 Claims, 8 Drawing Sheets

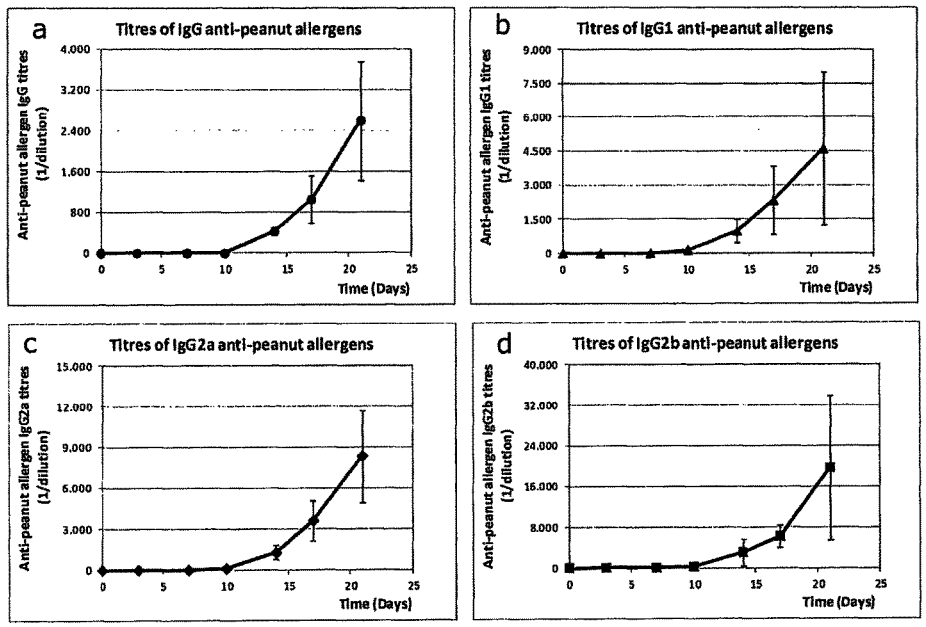
Fig.13a-d
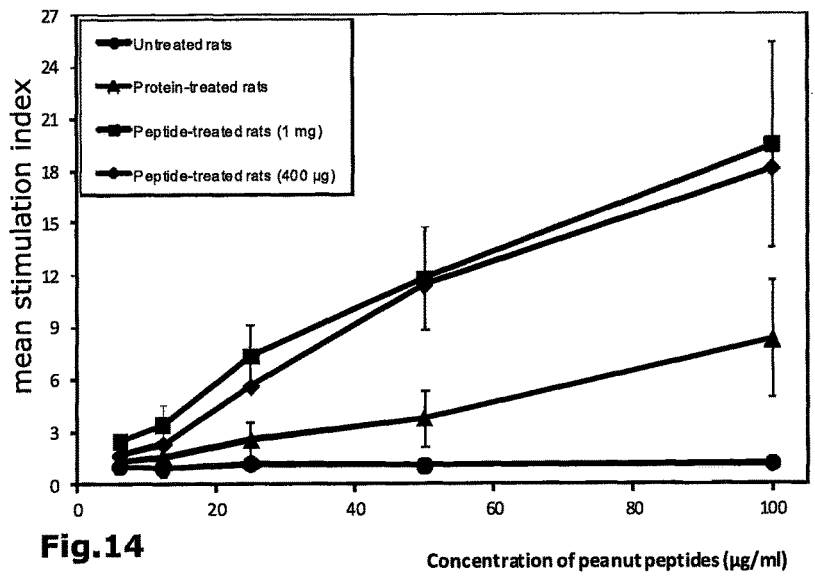
Fig.14

METHOD FOR THE PRODUCTION OF HYDROLYZED ALLERGENS

This application is a national stage entry of International Application No. PCT/EP2012/061404, filed Jun. 15, 2012, which claims priority to European Application No. 11170031.6, filed Jun. 15, 2011, each of which is incorporated by reference in its entirety.

The present invention is related to a method for the production of hydrolyzed allergens, more precisely to hydrolyzed allergens with a reduced allergenicity.

A general method for the production of hydrolyzed allergens is known from WO 2008/000783 A1. The method disclosed therein comprises the steps of extracting, purifying, denaturing and hydrolyzing of different natural materials like milk, venom, egg, weed, grass, tree, shrub, flower, vegetable, grain, fungi, etc.

However, advanced experimental studies by using the known method show that hydrolyzing of allergen proteins is complex and requires further procedural steps in order to hydrolyze the allergen proteins completely.

It is an object of the present invention to overcome at least some of the drawbacks of prior art, especially to provide antigens from natural allergens with a significantly reduced capability to trigger allergenic reactions compared to the crude allergen extract, but able to stimulate B-cells and T-cells.

The object is solved by a method for the production of hydrolyzed allergens from allergens comprising the steps of:
a) extracting a source of allergens comprising allergenic proteins to form an extract,
b) purifying the extract to remove non-protein components to form a purified extract,
c) denaturing the purified extract with a first denaturing agent to form a purified denatured extract,
d) refining the purified denatured extract to remove impurities to form a refined denatured extract,
e) denaturing the refined denatured extract with a second denaturing agent to form denatured allergen mixture, and
f) hydrolyzing the denatured allergen mixture to form the hydrolyzed allergens.

Surprisingly, it could be shown that applying two steps of denaturation, allergen proteins can be completely hydrolyzed.

"Extracting" as used herein is a treatment of an allergen source with an extraction medium including water, buffer or organic solvents to separate soluble ingredients from a non-soluble residue. The use of aqueous systems (comprising at least 50% $H_2O$) is preferred.

"Denaturating" as used herein is a process in which the proteins lose their quaternary, tertiary and secondary structure, especially this term refers to the treatment with one or several denaturing agents.

Step a) is an extracting step.

Extraction is preferably performed with aqueous solutions. Suitable salts are salts such as, but not restricted to disodium hydrogen phosphate, carbonate, bicarbonate, phosphate, acetate, TRIS and HEPES.

Also in contrast to many other extraction methods, it is preferred that the amount of extraction medium is comparatively large, i.e. at least 20 times the weight of the source of allergens, preferably 100 times the weight or more.

The extract is designated in the figures and examples as crude protein extract.

Step b) is a purification step.

After extraction of the source of allergens, i.e. step a), the extract is purified (step b) to remove non-protein components such as sugars, lipids, nucleic acids and the like.

Purifying of the extract may be performed by one or more of the following:
ion exchange chromatography steps (including anion exchange chromatography and cation exchange chromatography),
size exclusion chromatography steps (also called gel filtration),
precipitation steps,
hydrophobic interaction chromatography steps,
pseudo-affinity and affinity chromatographies and/or
diafiltration.

In a preferred embodiment ion exchange chromatography is used wherein in case of a cation exchanger the loading solution has a pH between the pKa of the acidic function of the cation exchanger and the pKa of the protein having the lowest pKa of the proteins in the extract. In case of an anion exchanger the pH is between the pKa of the basic function of the anion exchanger and the pKa of the protein having the highest pKa of the proteins constituting the extract.

Through this method all proteins bind to the ion exchanger while the neutral impurities and the impurities with the same charge as the ion exchange resin will be removed.

Alternatively, the allergen proteins can be precipitated by the addition of at least 50% (w/v) ammonium sulphate, more preferably of at least 90% (w/v) ammonium sulphate. In a preferred embodiment, the precipitation can also be performed by the addition of at least 2% (w/v) trichloroacetic acid (TCA), preferably 5% (w/v), more preferably of at least 10% (w/v) of TCA.

Typically, several different proteins are present in the protein fraction of the purified extract. The relative amounts of the proteins in the purified extract can be easily measured using methods like SDS-PAGE followed by densitometry.

Step c) is the first denaturation step.

As a next step (step c)) a denaturation is performed. The denaturing agent is preferably a chaotropic agent, a reducing agent or a mixture thereof. Suitable chaotropic agents are for example urea and guanidinium chloride. Typical reducing agents are for example dithiotriethol, β-mercaptoethanol, thio-glycerol, tris (2-carboxyethyl) phosphine (TCEP) and mixtures thereof.

A typical pH value is between 7.0 and 11.0, preferably between 7.0 and 10.0, more preferably between 7.0 and 9.0 for the first denaturation step.

Denaturing is preferably performed for at least 15 minutes, preferably at least 30 minutes and more preferably at least 60 minutes at a temperature between 15 and 40° C., preferably between 20 and 37° C.

In a preferred embodiment the reducing agent used for the denaturation is DTT (Dithiothreitol).

A suitable concentration of urea is 3 M or more, preferably 4 M or more. A suitable concentration of guanidinium is preferably 2 M, preferably 3 M or more.

Step d) is a purification step.

As step d) a further purification is performed. In a preferred embodiment gel filtration or diafiltration procedures will be applied. Use of chromatography, especially size exclusion chromatography is preferred. It is believed that by step d) further purification impurities which were not covalently bound to the protein components of the allergens and have been separated from the proteins by step c) can now be removed from the preparation.

Step e) is the second denaturation step.

After the step d), a second denaturing step is performed (step e)). For this denaturing step a second denaturing agent is used which can be the same or have different composition from step c). In a preferred embodiment the reducing agent used for the second denaturation step is TCEP.

It is preferred that the pH for the second denaturing step is set between 1.5 and 9.0. Preferably the pH is close to the optimum pH activity of the selected enzyme used in step f). In a preferred embodiment the pH is lower than 7.0 or lower than 5.0 or lower than 3.0 but preferably higher than 1.0. Denaturing is preferably performed for at least 15 minutes, preferably at least 30 minutes and more preferably at least 60 minutes at a temperature between 15 and 40° C., preferably between 20 and 37° C.

The next step (step f)) is a hydrolyzing step.

The hydrolyzing step is typically performed with an enzyme. Suitable enzymes are for example pepsin, trypsin, and/or chymotrypsin. The hydrolyzing step can be performed in the presence of a chaotropic agent, preferably urea or guanidinium chloride, too. During hydrolyzing, the concentration of urea and guanidinium chloride should be below 4 M, preferably below 3 M. The hydrolyzing step can also be performed in presence of a reducing agent, preferably TCEP. During hydrolysis, the concentration of TCEP is preferably below 10 mM. Preferably, pepsin is used. More preferably, pepsin at a pH range of 1.0-3.0 is used.

Step g) is a purification and selection of the hydrolyzed allergens.

In a further step (step g), the hydrolyzed allergens can be purified to form a purified hydrolysate, wherein specifically fragments of peptides, i.e. typically fragments with molecular weights below 1.000 Da, and, for instance, non-hydrolyzed fragments of proteins and/or peptides with molecular weights above 10.000 Da are removed. The peptides of the purified hydrolysate, therefore, comprise peptides with molecular weights between 1.000 and 10.000 Da. Preferably, less than 10% of the peptides have a molecular weight above 10.000 Da and less than 20% of the peptides have a molecular weight below 1.000 Da so that 70%, or more preferably 80% of the peptides are between 10.000 Da and 1.000 Da.

Suitable methods for removing large or small peptides are ultrafiltration and size exclusion chromatography. Again this size exclusion chromatography may be performed in the presence of chaotropic agents, for example urea, guanidinium chloride, ethylene glycol, isopropanol and mixtures thereof.

Preferably, the purification of the hydrolyzed peptides is performed by size exclusion chromatography and/or by ultrafiltration, wherein the size exclusion chromatography step is preferably performed in the presence of chaotropic agents, preferably selected among urea, guanidinium chloride, ethylene glycol, isopropanol and mixtures thereof.

One advantage of the hydrolysate is that the peptides are the digestion result of purified denatured proteins. They have a reduced potency to induce immediate allergic reactions and co-inflammatory reactions as well.

In a preferred embodiment of the present invention, the source of allergens is a natural source comprising milk, venom, egg, weed, grass, tree, shrub, flower, vegetable, grain, fungi, fruit, berry, nut, seed, bean, fish, shellfish, seafood, meat, spices, insect, mite, mould, animal, pigeon tick, worm, soft coral, animal dander, nematode, *Hevea brasiliensis* and mixtures thereof.

Preferred allergens used in this invention are especially grass pollen, house dust mite, birch pollen and peanuts.

Alternatively, synthetic sources of allergens as starting materials can be used. Synthetic sources of allergens means biotechnological produced proteins like recombinant proteins and/or genetically modified organisms.

In a more preferred embodiment of the present invention, peanuts and House Dust Mites (purified mites) are the source of allergens.

Preferably, the source comprises a mixture of allergens.

Preferably, the peanuts are selected among the *Arachis* genus, preferably from *hypogaea* species, more preferably from *hypogaea* and *fastigiata*. Sub-species comprise *Virginia, Spanish, Valencia* varieties and/or hydrids such as *Runner* or even transgenic peanuts obtained by genetic engineering.

Preferably, a mixture of at least 2, preferably 3 species/sub-species/varieties/hybrids and/or transgenic peanuts is used. In a preferred embodiment the red seed coat (tegument) of the peanuts has been removed.

The hydrolyzed allergens of the present invention can be used for the preparation of a pharmaceutical composition and/or food composition for inducing tolerance and desensitization. Induction of tolerance can be used to cure or prevent allergic reactions.

The allergic reaction to be treated or prevented depends on the source of allergens, i.e. allergy to peanuts are prevented or treated by using allergens from peanuts, whereas allergy to grass pollen are treated with allergens from grass pollen.

A further embodiment of the present invention is a pharmaceutical composition comprising the hydrolyzed allergens of the present invention. Additionally, the pharmaceutical composition may comprise one or more of the following substances: nucleoside triphosphates, nucleoside diphosphates, nucleoside monophosphates, nucleic acids, peptide nucleic acids, nucleosides or analogs thereof, immunosuppressive cytokines, compounds inducing expression of immunoproteasomes, 1,25-dihydroxyvitamin D3 or analogs thereof, lipopolysaccharides, endotoxins, heat shock proteins, thioredoxin with either NADPH or NADP-thioredoxin reductase, reducing agent, dithiothreitol, adrenergic receptor agonists such as salbutanol, adrenergic receptor antagonists such as butoxamine, compounds that regulate the expression of the adhesion molecule ICAM-1, N-acetyl-L-cysteine, y-L-glutamyl-L-cysteinyl-glycine (reduced L-glutathione), alpha-2-macroglobulins, inducers for Foxp3 gene expression, flavonoids, isoflavonoids, pterocarpanoids, stilbenes such as resveratrol, tachykinin receptor antagonists, chymase inhibitors, vaccine adjuvant or immunomodulators like CpG, aluminum hydroxide, calcium phosphate, TLR-4 agonists (i.e. MPL) and TLR-9 agonists or tolerogenic adjuvant like zymosan, beta-1,3-glucan, regulatory T-cell inducer, a muco-adhesive agent for attaching the particle to the intestinal mucosal lining such as a plant lectin, zinc, zinc salts, polysaccharides, vitamins and bacterial lysates or particles displaying surface linked antibodies.

In a preferred embodiment, the pharmaceutical composition is prepared for subcutaneous administration, nasal administration, epicutaneous administration, intralymphatic administration, oral administration, for sublingual drug delivery, or for enteric drug delivery.

One further embodiment of the present invention are purified hydrolyzed allergens obtainable by the method of the present invention.

A further embodiment of the present invention is the use of trichloroacetic acid as a precipitation means for the precipitation of allergenic proteins.

DESCRIPTION OF THE FIGURES

FIG. 13 a-d: Isotype profiles of the IgG antibody response of Lewis rats immunized subcutaneously with peanut peptides (1 mg/injection at D0, D3, D7) emulsified with Incomplete Freund Adjuvant (v/v). The results are expressed as the mean±SD (n=4).

FIG. 14: Splenocyte proliferation assay for Lewis rats previously immunized subcutaneously with peanut proteins (100 µg/injection) or peanut peptides (400 µg or 1 mg/injection) in response to increasing doses (from 6.25 to 100 µg/ml) of peanut peptides.

The invention is explained in more details by the following examples.

EXAMPLE 1

Peanut Allergens

Extraction of Peanut Allergens

A mix of three peanut types (*Arachis hypogaea* species *Runner*, *Virginia* and *Spanish* were peeled, grinded and mixed. A 2% (w/v) of the mix of peanuts was added to sodium phosphate (12.5 mM) and incubated 1 h under stirring at room temperature. The solution was then clarified and filtrated by adding Celite at 2% (w/v) and passing through a 0.45 µm filter. This sample constitutes the crude protein extract.

The presence of allergens in the crude protein extract was analyzed by Western-Blot using peanut allergic patient sera.

Figure 1:
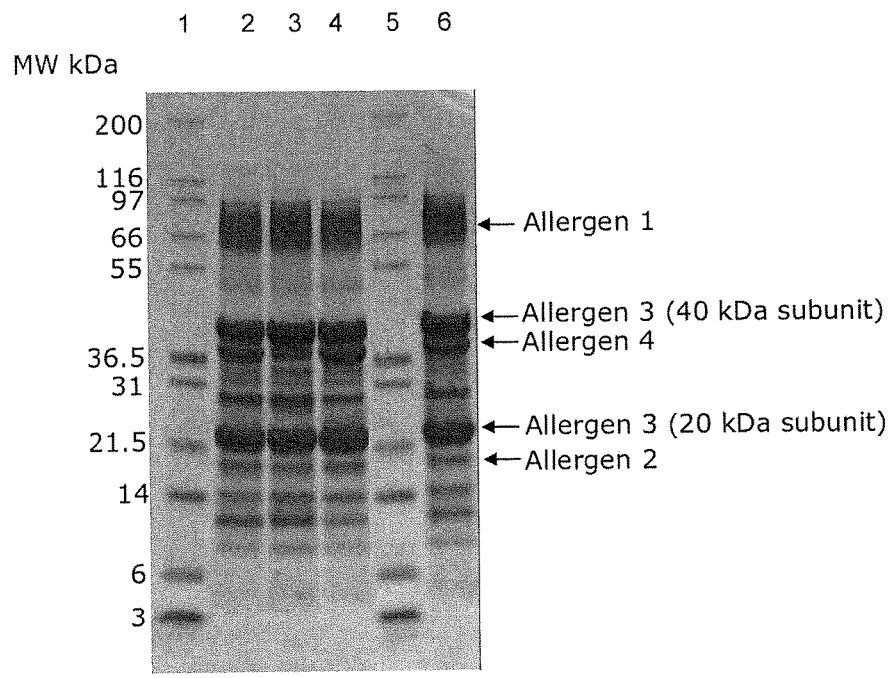
FIG. 1: Protein profile of peanut crude extract by SDS-PAGE. 4 to 12% Bis-Tris gel. Lane 1-5: Molecular weight markers, lane 2: crude protein extract of *Runner* type (13 µg), lane 3: crude protein extract of *Virginia* type (13 µg), lane 4: crude protein extract of *Spanish* type (13 µg), lane 6: crude protein extract of peanut mix (13 µg). Staining performed with Coomassie brilliant blue R-250. Allergens: allergen 1: ±60 kDa; allergen 2: ±2 kDa; allergen 3: 2 subunits±20 kDa and ±40 kDa; allergen 4: ±37 kDa.

As shown in FIG. 1, there are four major allergens in the crude protein extract (allergen 1, allergen 2, allergen 3 and allergen 4).

Purification of Peanut Allergen Proteins

The allergen extract was purified by:

Trichloroacetic acid precipitation

This step was performed at room temperature (20 to 25° C.).

10% (w/v) trichloroacetic acid was added to the product under stirring. Then, the precipitated extract was centrifuged during 15 minutes at 10.000 g. The supernatant was carefully discarded.

First Denaturation

The pellets were resuspended at 25 mg/ml in 8 M Urea, 0.1 M Tris-HCl, pH 8.0 and 80 mM DTT were added. The solution was incubated at 37° C. for 1 h.

Size exclusion chromatography on a G25 resin column (fine Sephadex from GE Healthcare)

The purified denatured extract was immediately loaded on the column and the proteins were eluted with 2 M Urea, 0.1 M Tris-HCl, pH 8.0.

The presence of proteins was followed by the absorbance at 280 nm. The fractions of interest were pooled to constitute the refined denatured extract.

Figure 2:
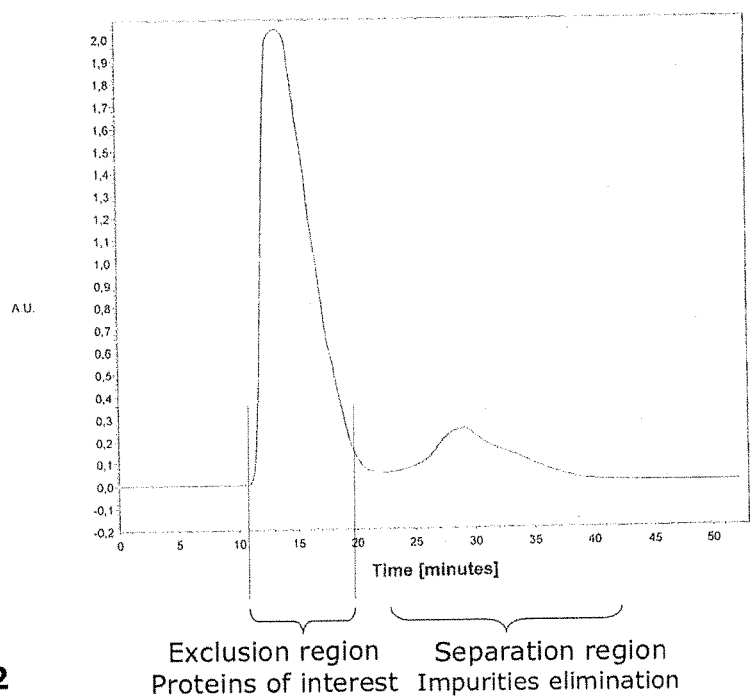
FIG. 2: SEC G 25 elution profile. The ratio column volume/sample volume was 7. The resin was equilibrated with 2 M urea, 0.1 M Tris-HCl, pH 8.0 at a flow rate of 10 ml/min. The elution was followed by the absorbance at 280 nm.

FIG. 2 illustrates the SEC G25 elution profile followed by the absorbance at 280 nm.

The refined denatured extract was further analyzed by SDS-PAGE and by Western Blotting using peanut allergic patient sera.

Figure 3:
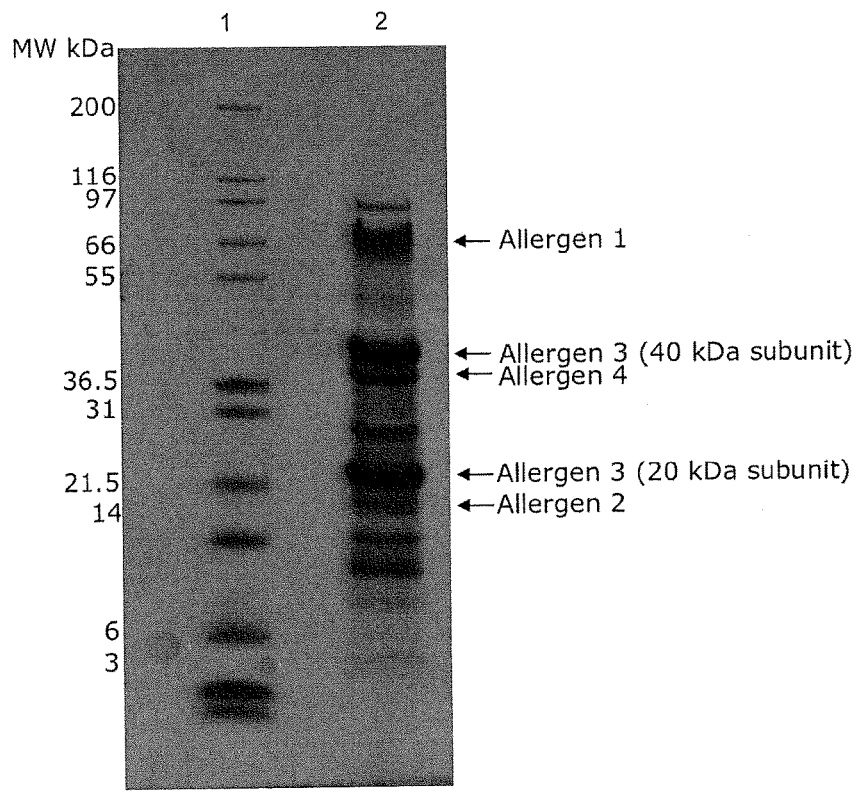
FIG. 3: Protein profile of purified allergen extract by SDS-PAGE. 4-12% Bis-Tris gel. Lane 1: molecular weight markers, lane 2: purified denatured extract (13 µg). Staining performed with Coomassie brilliant blue R-250. Allergen 1: ±60 kDa; allergen 2: ±2 kDa; allergen 3: 2 subunits±20 kDa and ±40 kDa; allergen 4: ±37 kDa.

As shown in FIG. 3, the four major allergens visualized in the extract by SDS-PAGE (cf. FIG. 1) are present in the purified denatured extract.

Figure 4:
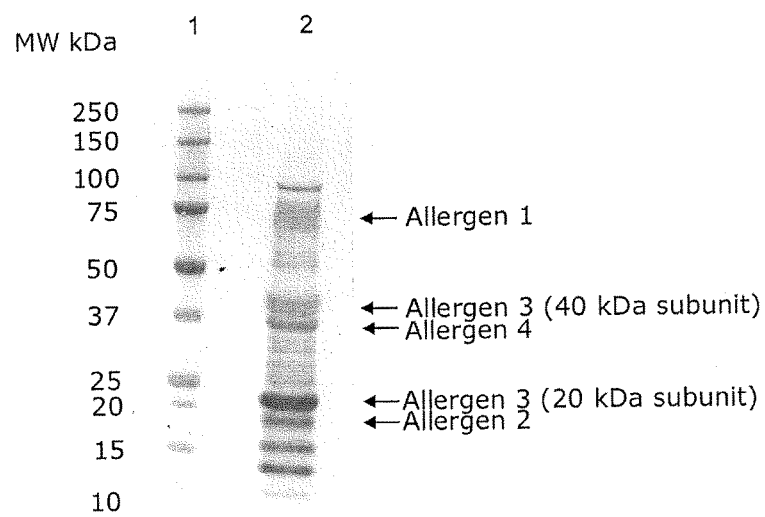
FIG. 4: Immuno reactivity by IgE western-blot. Lane 1: molecular weight markers, lane 2: purified denatured extract (13 µg). Membrane blocked by BSA 2% (w/v). Pool of 6 patient sera diluted to 1/500. IgE binding detected by goat antihuman IgE peroxidase conjugate diluted to 1/1.000 and revealed by TMB substrate. Allergen 1: ±60 kDa; allergen 2: ±2 kDa; allergen 3: 2 subunits±20 kDa and ±40 kDa; allergen 4: ±37 kDa.

FIG. 4 shows that all proteins and in particular the four major allergens are recognized by peanut allergic patient sera and then visualized with anti-human IgE antibodies.

Second Denaturation:

8 M urea and 40 mM TCEP were added to the refined denatured extract. Then, the pH was adjusted to 2.5. The solution was incubated at 37° C. for 1 h.

Hydrolysis of the Denatured Peanut Allergens

The denatured allergens were hydrolyzed using the following protocol:

The denatured allergen mixture were diluted 4-fold with 10 mM HCl and acidified with HCl 6 N to pH 2.0. The protein hydrolysis was performed with 16 Eu.Ph.U of pepsin for 100 mg of proteins at 37° C., during 2 h. The hydrolysis was stopped by raising the pH to 10.0 with NaOH solution.

Figure 5:
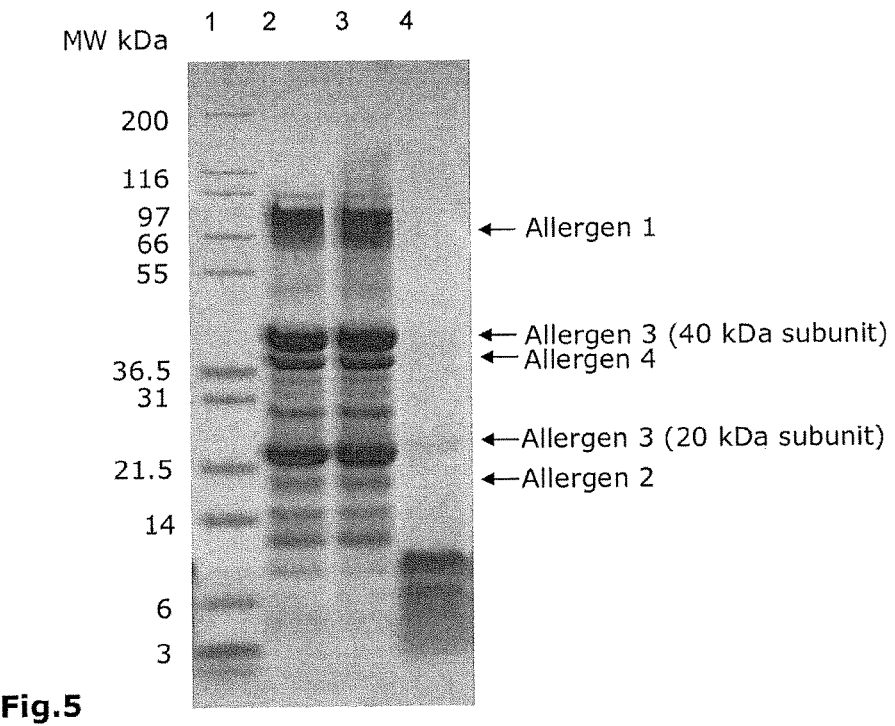
FIG. 5: Hydrolysis profile of proteins denatured twice by SDS-PAGE. 4-12% Bis-Tris gel. Lane 1: molecular weight markers, lane 2: crude protein extract (13 µg), lane 3: denatured allergen mixture (13 µg), lane 4: hydrolyzed allergens (26 µg). Staining performed with Coomassie brilliant blue R-250.

FIG. 5 shows a comparison between the crude protein extract (lane 2), the denatured allergen mixture (lane 3) and the hydrolyzed allergens (lane 4). It can be seen, proteins denatured twice are almost totally hydrolyzed since only one residual peptide band above 10 kDa is visualized on the profile.

Figure 6:
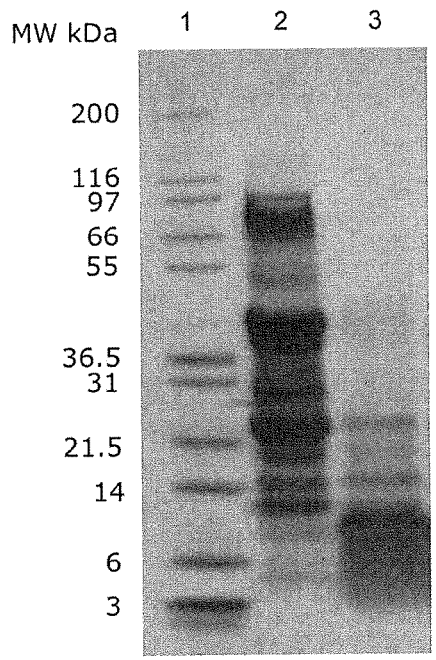
FIG. 6: Hydrolysis profile of proteins denatured once by SDS-PAGE. 4-12% Bis-Tris gel. Lane 1: molecular weight markers, lane 2: crude protein extract (13 µg), lane 3: hydrolysate of proteins denatured once (26 µg), Staining performed with Coomassie brilliant blue R-250.

In comparison thereto, FIG. 6, especially lane 3, shows the case of proteins denatured once. Three residual proteins are visualized on the profile of the corresponding hydrolysate. This illustrates the benefit of the double denaturation since the hydrolysis is less efficient when proteins are denatured only one time.

Purification of Hydrolyzed Peanut Allergens

Figure 7:
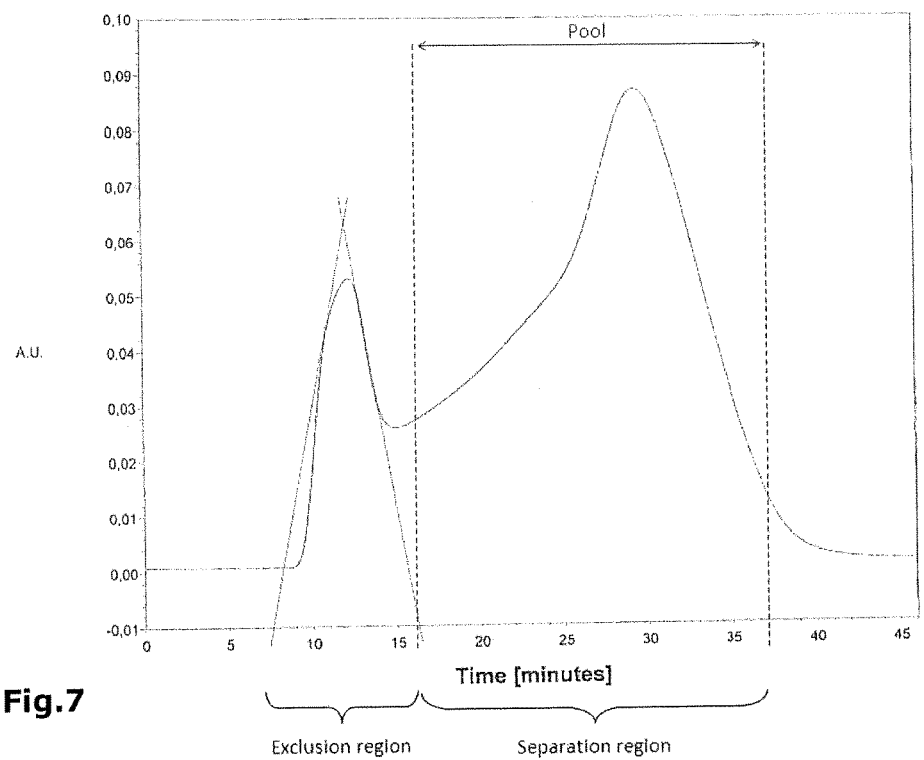
FIG. 7: G 50 SEC elution profile. The column was equilibrated with 2 M urea, 0.1 M Tris-HCl, pH 9.5 at a flow rate of 10 ml/min. The ratio column volume/sample volume was 10. The elution was followed by the absorbance at 280 nm.

In order to eliminate the peptides with a MW ≥10.000 Da and MW ≤1.000 Da, the hydrolyzed allergens were purified by:

Size exclusion chromatography on G50 resin (fine Sephadex from GE Healthcare). After increasing pH, the hydrolyzed allergens were rapidly loaded on the G50 column. The peptides were eluted with 2 M Urea, 0.1 M Tris-HCl, pH 9.5. The elution was followed by the absorbance at 280 nm. The fractions containing the peptides (MW ≤10 kDa) were pooled as shown in FIG. 7.

Diafiltration on 1 kDa membrane (ultrafiltration cassette Omega PES from PALL). The peptides were concentrated 25-fold, diafiltrated against 10 volumes of 50 mM sodium phosphate at pH 7.6 and finally concentrated 2-fold. This sample constitutes the purified hydrolysate.

Figure 8:
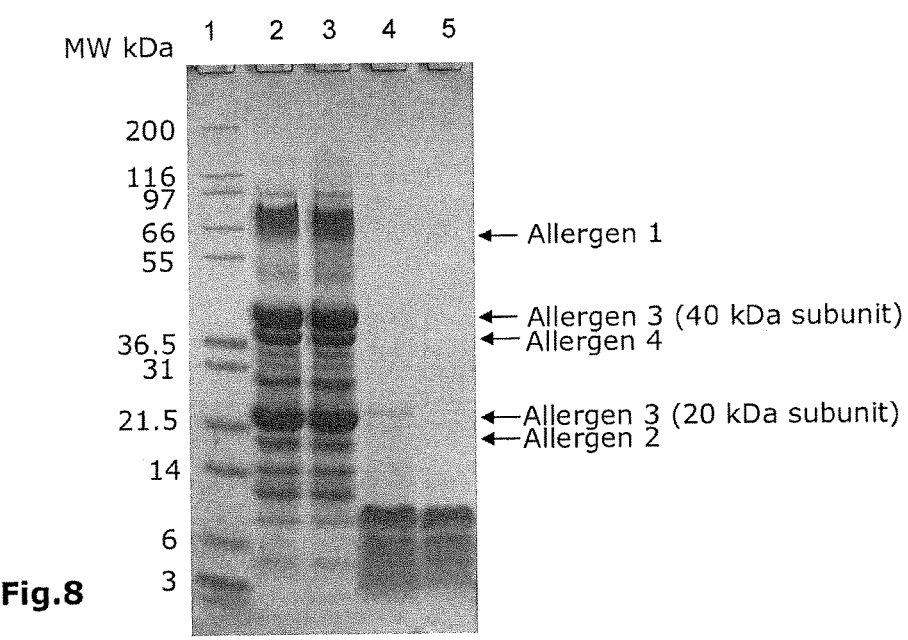
FIG. 8: Comparison of the peptide profiles before and after purification. The analysis was performed by SDS-PAGE. 4-12% Bis-Tris gel. Lane 1: molecular weight markers, lane 2: crude protein extract (13 µg), lane 3: denatured allergen mixture (13 µg), Lane 4: hydrolyzed allergens (26 µg), lane 5: purified hydrolysate (26 µg). Staining performed with Coomassie brilliant blue R-250.

The purified hydrolysate was analyzed by SDS-PAGE (see FIG. 8). The profile (lane 5) shows that there are no residual proteins with molecular weights above 10 kDa.

The efficiency of the purification was controlled by size exclusion HPLC. A BioSep-SEC S2000 column was equilibrated with 50 mM $Na_2HPO_4$, 0.5% (w/v) SDS, pH 6.8 at a flow rate of 1 ml/min. The peptides were detected at 215 nm.

Figure 9:
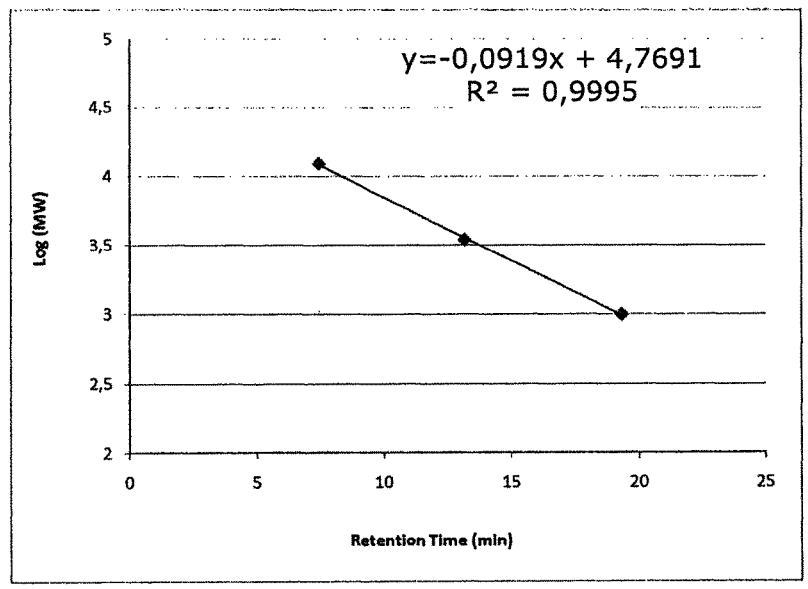
FIG. 9: Calibration curve for HPLC analysis. 10 µl of the following standards (1 mg/ml) were injected onto the Bio-Sep-SEC S 2000 column: CytoChrom c (12 kDa), Glucagon (3.5 kDa), 1 kDa synthetic peptide.

The 10 kDa and 1 kDa limits were calculated from a calibration curve as exemplified in FIG. 9.

Figure 10:
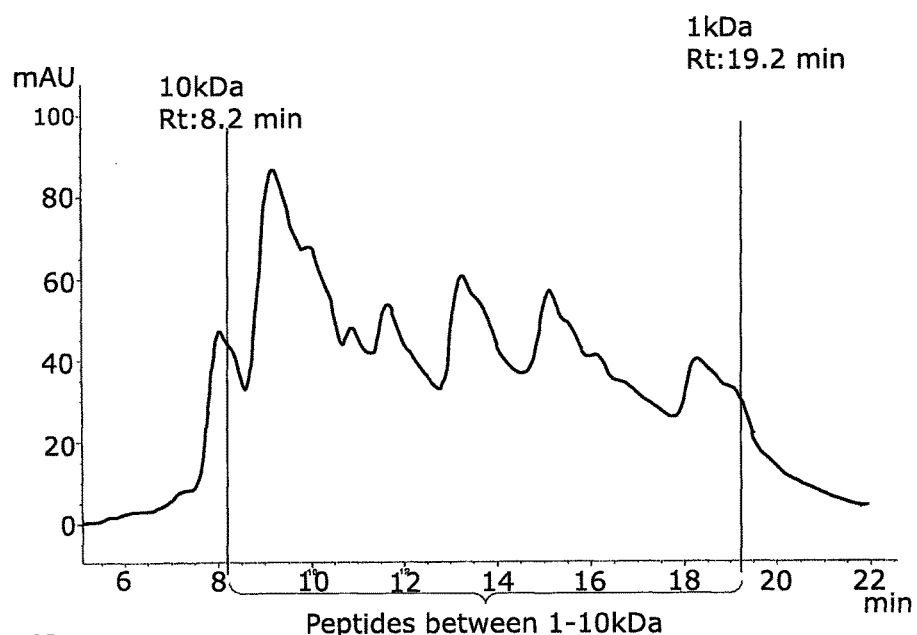
FIG. 10: Size exclusion HPLC profile. Column: BioSep-SEC S 2000. Elution buffer: 50 mM $Na_2HPO_4$, 0.5% (w/v) SDS-pH 6.8. Flow rate 1 ml/min. Detection at 215 nm. 10 µl of the sample were injected.

As shown in FIG. 10, peptides with molecular weights between 1.000 Da and 10.000 Da represent about 80% of all peptides in the purified hydrolysate.

EXAMPLE 2

Allergens from House Dust Mite
*Dermatophagoides pteronyssinus*

Protein Extraction of House Dust Mite

Proteins from House Dust Mite were extracted by incubation in Phosphate Buffer Saline pH 7.4 during 1 h at room temperature under stirring. The solution was clarified and filtrated by adding Celite at 2% (w/v) and passing through a 0.45 μm PVDF filter. This sample constitutes the crude protein extract.

The crude protein extract seems to show the major allergens (Derp1, Derp2) which can be localised according to their molecular weight (25 kDa and 14 kDa respectively).

Purification of Allergen Proteins from House Dust Mite

The purification was performed by:

Trichloracetic acid precipitation

10% (w/v) trichloracetic acid was added to the crude protein extract under stirring for 5 min at room temperature. The proteins were collected by centrifugation during 20 min at 10.000 g.

First denaturation

After elimination of the supernatant, the pellet was resuspended in 8 M urea, 0.1 M Tris pH 7-8. The solution was incubated for 1 h at 37° C. after pH adjustment to 7.5 and addition of 80 mM DTT.

Size exclusion chromatography on G25 resin column

The proteins from the denaturated extract were loaded on the column, and eluted with 2 M Urea, 0.1 M NaCl pH 9.0.

The presence of proteins was monitored by the measurement of the absorbance at 280 nm.

Second denaturation

The denaturation occurred by incubation at 37° C. for 1 h in 4 M urea, 0.1 M NaCl and 40 mM TCEP with the pH adjusted to 2.5.

Hydrolysis of the Denaturated Allergens for House Dust Mite

The denaturated protein mixture was previously diluted 2-fold with 10 mM HCl and acidified with HCl 6N to pH 2.0. The hydrolysis of proteins was conducted with 16 Eu.Ph.U of pepsin per 100 mg for 1 h at 37° C.

Figure 11:
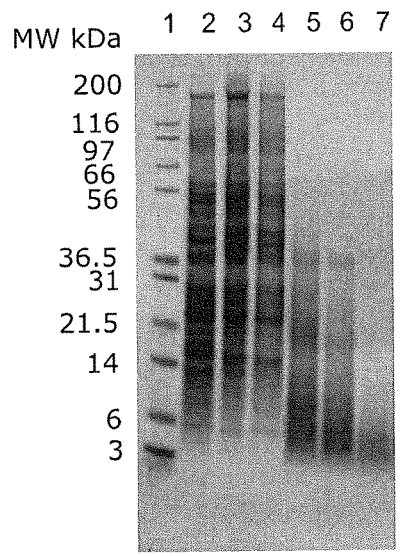
FIG. 11: Profile of House Dust Mite proteins on 4 to 12% Bis-Tris reducing SDS-Page at different steps of purification. Lane 1: Molecular weight markers; Lane 2: crude protein extract from *Dermatophagoides pteronyssinus*; Lane 3: Protein profile obtained after TCA precipitation; Lane 4: Purified denaturated extract obtained after the second denaturation with TCEP; Lane 5: Profile of denaturated proteins hydrolyzed with 0.4 Eu. Ph. U of pepsin/100 mg; Lane 6: Profile of denaturated proteins hydrolyzed with 4 Eu. Ph. U of pepsin/100 mg. Lane 7: Profile of denaturated proteins hydrolyzed with 16 Eu. Ph. U of pepsin/100 mg. Staining performed with Coomassie brilliant blue R-250.

FIG. 11 shows a profile of House Dust Mite proteins on 4 to 12% Bis-Tris reducing SDS-Page at different steps of purification.

Lane 1: Molecular weight markers;
Lane 2: crude protein extract from *Dermatophagoides pteronyssinus*;
Lane 3: Protein profile obtained after TCA precipitation;
Lane 4: Purified denaturated extract obtained after the second denaturation with TCEP;
Lane 5: Profile of denaturated proteins hydrolyzed with 0.4 Eu.Ph.U of pepsin/100 mg;

Lane 6: Profile of denatured proteins hydrolyzed with 4 Eu.Ph.U of pepsin/100 mg.

Lane 7: Profile of denatured proteins hydrolyzed with 16 Eu.Ph.U of pepsin/100 mg. Staining performed with Coomassie brilliant blue R-250.

EXAMPLE 3

With a method similar to example 2, hydrolyzed allergens of grass and birch pollen were prepared.

EXAMPLE 4

Peanut Peptides: Allergenicity, Immunogenicity and Blocking Potential of Specific Antibodies The allergenicity of peanut peptides was investigated by analysis of their in vitro IgE-binding properties by an ELISA inhibition assay.

T cell proliferation, specific IgG-titres following rat immunization were used to address their immunogenicity.

The blocking activity of the antibodies generated to peanut peptides was assessed by a competition ELISA.
Allergenicity of Peanut Peptides: Reduced Binding of IgE from Serum of Allergic Patients Peanut peptides exhibit reduced allergenicity in vitro as demonstrated by an ELISA inhibition assay.

The principle of the ELISA inhibition assay was to measure the decrease of the binding to peanut proteins of IgE from serum of allergic patients previously incubated with increasing amounts of either peptides or proteins from peanuts.

Maxisorp 96 well microtitre plates were coated with 0.8 µg/ml of peanut proteins in 0.1M carbonate-bicarbonate Buffer pH 9.6 overnight at 4° C. After blocking for 1 h at 37° C., wells were incubated overnight at 4° C. with 100 µl of mixtures of the serum pool (1/50 dilution) of peanut allergic patients previously treated (1 h at 37° C.) with serial dilutions of peanut proteins (range: 1.25 µg/ml to 63.5 µg/ml) or peanut peptides (range: 50 µg/ml to 20 ng/ml). After washings, wells were incubated with peroxidase-labelled anti-human IgE antibodies, and developed by incubating with 100 µl of TMBS substrate. The reaction was stopped with 100 µl of 1M $H_3PO_4$ and the optical density values were measured at 450-650 nm.

The percentage of inhibition of IgE binding achieved by preincubation in presence of peanut peptides or peanut proteins was calculated as follow:

% inhibition=100−[[OD of the inhibed sample/mean OD of positive controls]×100]

Positive controls were 50 µl of pooled human serum diluted 1/25 mixed with 50 µl of rabbit preimmune serum (n=10).

Figure 12:
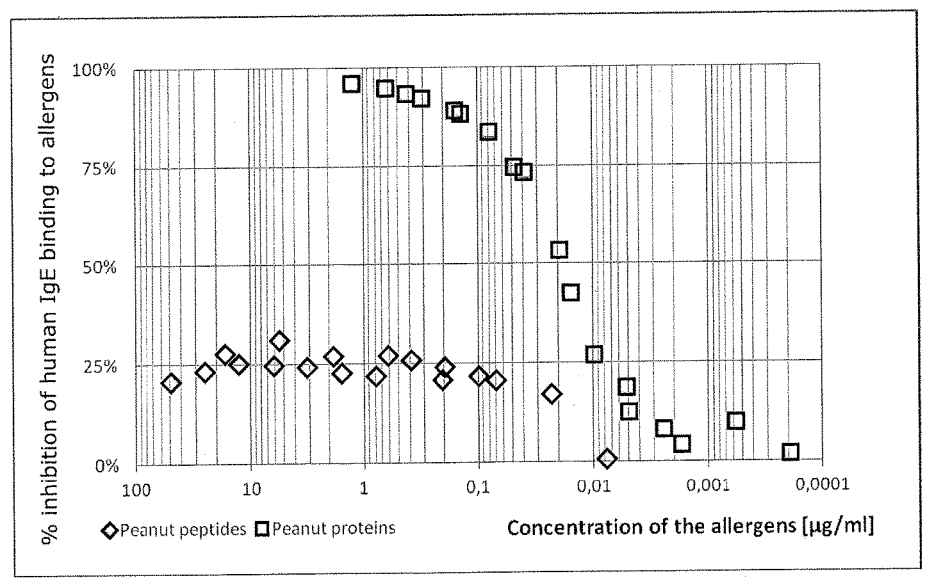
FIG. 12: Reduced allergenicity of peanut peptides. The binding of IgE from pooled sera of peanut-allergic donors to peanut allergens was more inhibited by preincubation with increasing amounts of peanut intact allergens than by peanut allergen peptides.

FIG. 12 shows a reduced allergenicity of peanut peptides. The binding of IgE from pooled sera of peanut-allergic donors to peanut allergens was more inhibited by preincubation with increasing amounts of peanut proteins than by peanut peptides.
Immunogenicity of Peanut Peptides: Induction of Specific Antibodies in Rats Peanut peptides are able to evoke humoral immune responses.

Rats that have been immunized subcutaneously three times with peanut peptides emulsified in Incomplete Freund Adjuvant produce significant levels of IgG. The mixture of peanut peptides induced IgG1, IgG2a and IgG2b.

At days 0, 3 and 7 (D0, D3, D7), a group of four seven week-old female rats were immunized with 1 mg of peanut peptides administered subcutaneously as an emulsion (v/v) with Incomplete Freund Adjuvant.

Maxisorp 96 well microtitre plates were coated with 2 µg/ml of peanut proteins in 0.1M carbonate-bicarbonate Buffer pH 9.6 overnight at 4° C. After blocking for 1 h at 37° C., wells were incubated 1 h at 37° C. with 100 µl of serial dilutions of serum (from 1/200 to 1/437.400 dilution) of treated rats. Bound rat IgG were detected with 1/20.000 diluted peroxidase-labeled anti-rat IgG. IgG1, IgG2a or IgG2b were detected with biotin-labelled antibodies diluted respectively 1/1.500, 1/500 and 1/500. After incubation with peroxidase-streptavidin (1/200), the color reaction was started by adding 100 µl of TMBS substrate. The reaction was stopped with 100 µl of 1M $H_3PO_4$ and optical density values were measured at 450-650 nm.

The results were expressed as titres. They were defined as the maximal dilution of rat antisera that gave absorbances of 0.3.

FIG. 13 a-d shows isotype profiles of the IgG antibody response of Lewis rats immunized subcutaneously with peanut peptides (1 mg/injection at D0, D3, D7) emulsified with Incomplete Freund Adjuvant (v/v). The results are expressed as the mean±SD (n=4).
Immunogenicity of Peanut Peptides: Stimulation of Cellular Immune Responses Peanut peptides are able to trigger the proliferation of T cells isolated from spleen of rats previously immunized with peanut peptides or peanut proteins.

Peanut peptides were compared to purified peanut proteins for their capacity to stimulate T lymphocytes by using a cell proliferation assay based on thymidine incorporation.

The study was conducted on seven week-old female Lewis rats.

At D0, D3 and D7, four rats were immunized intraperitoneally with 100 µg of peanut proteins mixed with alum (v/v). Four rats were treated with 400 µg or 1 mg of peanut peptides administered subcutaneously as an emulsion (v/v) with Incomplete Freund Adjuvant.

At D21, the animals were sacrificed and the splenocytes were withdrawn. Cells were cultured in RPMI 1640 supplemented with 10% (v/v) Foetal Calf Serum, 1% non-essential amino-acids, 2 mM L-glutamine, 1 mM pyruvate, 50 µM β-mercaptoethanol, 50 U/ml Penicillin, 100 µg/ml streptomycin, 10 µg/ml gentamicin, 1 mM HEPES (complete medium).

Cells were plated at a density of $2 \times 10^6$/ml in complete medium. Antigens, also in complete medium were used at the following concentrations: 100, 50, 25, 12.5, 6.25 µg/ml. All cultures were carried out in a humidified incubator at 37° C. in 5% $CO_2$. Proliferation assays were performed in triplicate in 96-well round-bottom plates for 4 days with cells being pulsed with 0.5 µCi of [$^3$H]-thymidine/well at 72 h, harvested 12 to 16 h later and counted for β-radioactivity.

The results were expressed as proliferation index calculated as follow:

Cells cultured in medium alone (non-stimulated cells) were considered as 0% of proliferation.

Proliferation index=Cpm tested well (mean of triplicates)/cpm (mean of triplicates) of medium-treated cells.

FIG. 14 shows a splenocyte proliferation assay for Lewis rats previously immunized with peanut proteins (100 µg/injection) or peanut peptides (400 µg or 1 mg/injection) in response to increasing doses (from 6.25 to 100 µg/ml) of peanut peptides.

Results are expressed as means±SD of triplicate stimulation index.

As shown on FIG. 14, peanut peptides were able to induce the proliferation of T cells from rats previously immunized with peanut proteins. Moreover, whatever the peanut peptide concentration in the culture medium, the T cell proliferation was higher when rats were previously immunized subcutaneously with peanut peptides in presence of Incomplete Freund Adjuvant.

For each doses of peanut peptides, untreated rats did not show any relevant proliferation.

Figure 15:
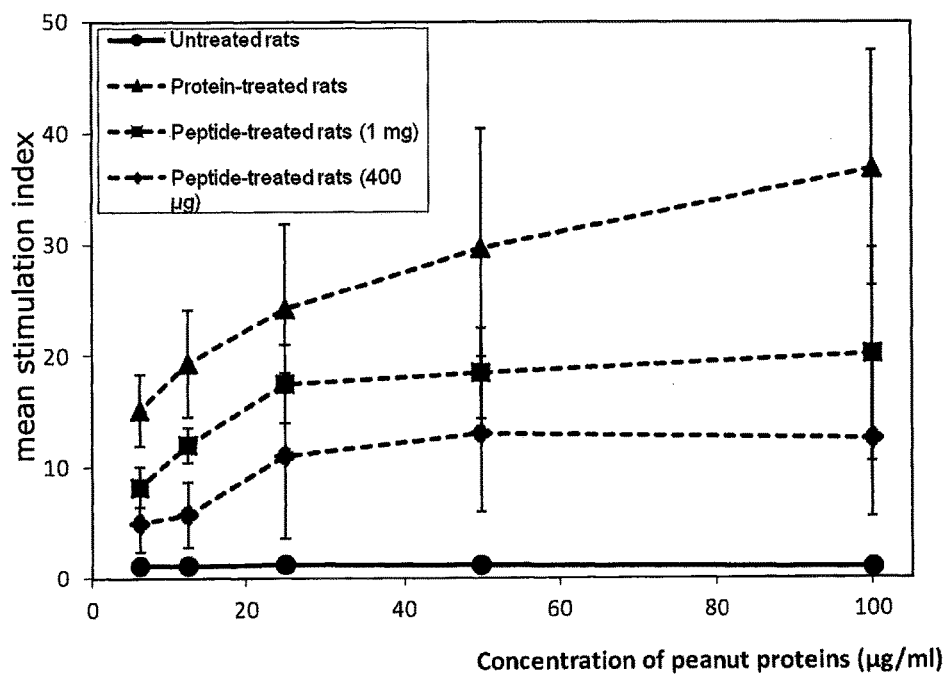
FIG. 15: Splenocyte proliferation assay for Lewis rats previously immunized subcutaneously with peanut proteins (100 µg/injection) or peanut peptides (400 µg or 1 mg/injection) in response to increasing doses (from 6.25 to 100 µg/ml) of peanut proteins.

FIG. 15 shows a splenocyte proliferation assay for Lewis rats previously immunized with peanut proteins (100 µg/injection) or peanut peptides (400 µg or 1 mg/injection) in response to increasing doses (from 6.25 to 100 µg/ml) of peanut proteins.

FIG. 15 displays the proliferation of T cells by increasing doses of purified peanuts proteins. Albeit to a lower level when compared to T cells from peanut protein immunized rats, the purified peanut proteins also triggered a specific immune response on T cells from rats immunized with peanut peptides administered subcutaneously.

Untreated rats did not show any relevant proliferation whatever the peanut protein concentration in the culture medium.

Results are expressed as the means±SD of triplicate stimulation index.

These results demonstrated that peanut peptides have conserved a biological activity linked to the presence of T cell epitopes, capable of stimulating specific immune responses in immunized animals.

Blocking Potential of the Antibodies Generated to Peanut Peptides

Immunoglobulins induced by immunization of rabbits with peanut peptides inhibit patient's IgE binding to protein allergens.

The ability of rabbit anti-peanut peptides and anti-peanut proteins to inhibit the binding of peanut-allergic patient's IgE antibodies to allergens was examined by ELISA competition experiments.

ELISA Maxisorp plates coated 2 h at 37° C. with 0.8 µg/ml of peanut proteins were incubated (v/v) with serial twofold dilutions of rabbit antiserum to peanut peptides or peanut proteins (from 1/2 to 1/1024 final dilution) in presence of pooled human serum diluted 1/50 (final dilution). After overnight incubation at 4° C., bound IgE antibodies were detected with 1/8.000 diluted peroxidase-coupled polyclonal anti-human IgE antibodies. The optical density values corresponding to bound IgE were measured at 450-650 nm. The percentage of inhibition of IgE binding achieved by preincubation in presence of serum from rabbit (anti-peanut peptides or anti-peanut proteins) was calculated as follow:

% inhibition=100−[[OD of the inhibed sample/mean OD of positive controls]×100]

Positive controls were 50 µl of pooled human sera diluted 1/25 mixed with 50 µl of rabbit preimmune serum (n=10).

Figure 16:
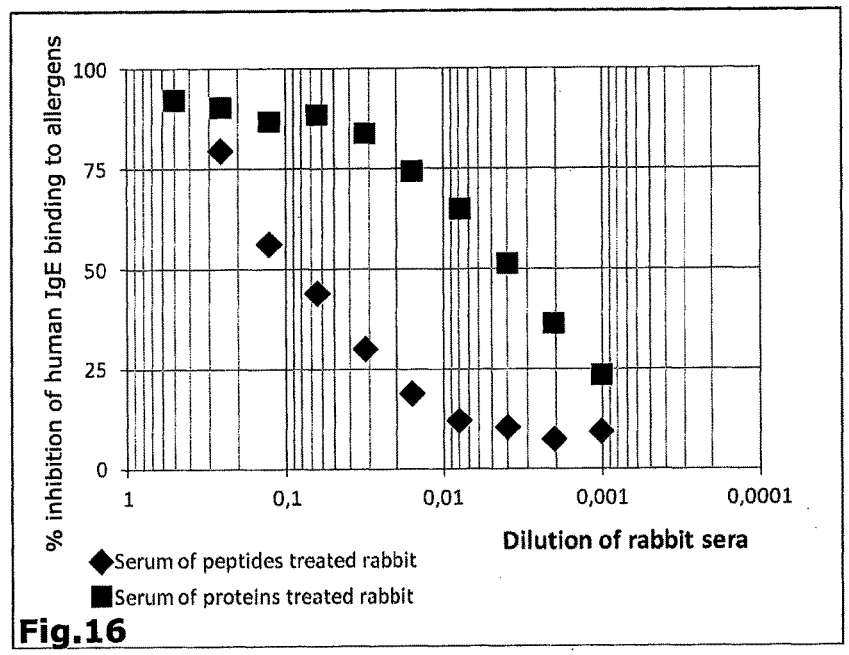
FIG. 16: Competition ELISA for assessment of blocking antibody activity. Peanut proteins were coated on microtitre plate. The pooled serum of peanut allergic patients were mixed with serial dilutions of rabbit antibodies generated to either peptides or proteins of peanuts. After incubation, the IgE that bind to the peanut proteins coated to the plate were detected using anti-human IgE labeled peroxydase antibodies.

FIG. 16 shows a competition ELISA for assessment of blocking antibody activity. Peanut proteins were coated on microtitre plate. The pooled serum of peanut allergic patients were mixed with serial dilutions of rabbit antibodies generated to either peptides or proteins of peanuts. After incubation, the IgE that bind to the peanut proteins coated to the plate were detected using anti-human IgE labeled peroxydase antibodies.

In conclusion, peanut peptides obtained by the present invention exhibit features favourable for their use in allergy immunotherapy. Indeed, they are characterized by reduced allergenicity but preserved T-cell reactivity. Moreover, the allergen-derived peptides are able to induce an immune response in animals and generate IgG antibodies with blocking potential on human IgE binding to the allergens.

The invention claimed is:
1. A method for the production of hydrolyzed allergens from allergens comprising the steps of:
    a) extracting a source of allergens comprising allergenic proteins to form an extract,
    b) purifying the extract to remove non-protein components to form a purified extract,
    c) denaturing the purified extract with a first denaturing agent at a pH of 7.0 to 11.0 to form a purified denatured extract,
    d) refining the purified denatured extract to remove impurities to form a refined denatured extract,
    e) denaturing the refined denatured extract with a second denaturing agent at a pH of 1.0 to 7.0 to form denatured allergen mixture,
    f) hydrolyzing the denatured allergen mixture to form the hydrolyzed allergens, and
    g) purifying the hydrolyzed allergens to remove peptides with molecular weights above 10,000 Da and below 1,000 Da, wherein 70% or more of the peptides are between 10,000 Da and 1,000 Da; wherein the first denaturing agent is a mixture of a chaotropic agent and a reducing agent and wherein the second denaturing agent is a mixture of a chaotropic agent and a reducing agent.

2. The method of claim 1, wherein extracting is performed in a solution comprising no salt or a salt selected from carbonate, bicarbonate, phosphate, acetate, TRIS and HEPES, wherein extracting is performed with an extraction medium.

3. The method of claim 1, wherein the purifying and/or refining comprises one or more of an ion exchange chromatography step, a gel filtration or size exclusion chromatography step, a hydrophobic interaction chromatography step, a pseudo affinity or affinity chromatography step.

4. The method according to claim 1, wherein the first and/or second denaturating agent comprises urea at a concentration of more than 4 M, and guanidinium chloride at a concentration above 3 M.

5. The method of claim 1, wherein hydrolyzing is performed with an enzyme.

6. The method of claim 1, wherein the removal of the peptides is performed by size exclusion chromatography and/or by ultrafiltration, wherein the size exclusion chromatography is performed in the presence of chaotropic agents.

7. The method of claim 1, wherein the sources of allergens are peanuts.

8. The method of claim 1, wherein denaturing is performed with a denaturing agent selected from the group of urea, guanidinium chloride, dithiotreitol, thiglycerol, β-mercaptoethanol, tris (2-carboxyethyl) phosphine (TCEP), and mixtures thereof.

9. The method of claim 1, wherein
    extracting is performed in a solution comprising phosphate, purifying or refining includes a precipitation step,
the precipitation step is performed with a solution comprising trichloroacetic acid,
denaturing is performed with a combination of urea and dithiotreitol,
the hydrolyzing is performed with pepsin,
the removal is performed by size exclusion chromatography in the presence of chaotropic agents, and
the source of allergens are peanuts from *Arachis hypogaea*.

10. The method of claim 1, wherein the second denaturing agent is tris(2-carboxyethyl)-phosphine (TCEP).

11. The method of claim 5, wherein the hydrolyzing is performed in the presence of a chaotropic agent and a reducing reagent.

12. The method of claim 7, wherein the source of allergens is a mixture of at least two species/subspecies/varieties/hybrids and/or transgenic peanuts.

13. The method of claim 12, wherein the peanuts are selected from the *Arachis* genus.

14. The method of claim 13, wherein the peanuts selected from the *Arachanis* genus are *hypogaea* or *fastigiata*.

* * * * *